(12) United States Patent
Plumas et al.

(10) Patent No.: US 7,341,870 B2
(45) Date of Patent: Mar. 11, 2008

(54) DENDRITIC CELL LINE

(75) Inventors: Joel Plumas, Grenoble (FR); Laurence Chaperot-Dubonnet, Francin (FR)

(73) Assignee: Etablissement Francais du Sang, Paris (FR)

( * ) Notice: Subject to any disclaimer, the term of this patent is extended or adjusted under 35 U.S.C. 154(b) by 24 days.

(21) Appl. No.: 10/536,318

(22) PCT Filed: Dec. 16, 2003

(86) PCT No.: PCT/FR03/03748

§ 371 (c)(1),
(2), (4) Date: Jun. 14, 2005

(87) PCT Pub. No.: WO2004/061089

PCT Pub. Date: Jul. 22, 2004

(65) Prior Publication Data

US 2005/0272151 A1  Dec. 8, 2005

(30) Foreign Application Priority Data

Dec. 16, 2002 (FR) .................................. 02 15927

(51) Int. Cl.
*G01N 33/53* (2006.01)
*C12N 5/02* (2006.01)
*C12N 5/08* (2006.01)
*A01N 63/00* (2006.01)

(52) U.S. Cl. ..................... 435/325; 435/7.22; 435/335; 435/339; 435/372; 435/375

(58) Field of Classification Search .................... None
See application file for complete search history.

(56) References Cited

U.S. PATENT DOCUMENTS 5,648,219 A  7/1997 MacKay et al.

7,038,029 B2 * 5/2006 Lopez .................. 536/23.1
2003/0148316 A1 * 8/2003 Lipford et al. ............. 435/6
2004/0006032 A1 * 1/2004 Lopez .................... 514/44

FOREIGN PATENT DOCUMENTS

WO  WO 02/40646 A1  5/2002
WO  WO 02/40647 A1  5/2002

OTHER PUBLICATIONS

Decker WK, Xing D, Shpall EJ. Dendritic cell immunotherapy for the treatment of neoplastic disease. Biol Blood Marrow Transplant. Feb. 20096;12(2):113-25. Review. □□*
Laurence Chaperot et al., "Identification of a leukemic counterpart of the plasmacytoid dendritic cells", 2001 by The American Society of Hematology, Blood, May 15, 2001, vol. 97, No. 10, pp. 3210-3217.
Andrzej Dzionek et al., "Plasmacytoid Dendritic Cells: From Specific Surface Markers to Specific Cellular Functions", American Society for Histocompatibility and Immunogenetics, 2002 Published by Elsevier Science Inc. Human Immunology 63, pp. 1133-1148 (2002).
Marina Cella et al., "Plasmacytoid monocytes migrate to inflammed lymph nodes and produce large amounts of type I interferon", Aug. 1999, 919-923, vol. 5, No. 8.
Jacques Banchereau et al., "Immunobiology of Dendritic Cells", Annu. Rev. Immunol. 2000., 18: pp. 767-811.
Ralph M. Steinman et al., "Exploiting dendritic cells to improve vaccine efficacy", The Journal of Clinical Investigation, Jun. 2002, vol. 109, No. 12, pp. 1519-1526.

* cited by examiner

*Primary Examiner*—Celine Qian
*Assistant Examiner*—Laura M Mitchell
(74) *Attorney, Agent, or Firm*—Oliff & Berridge PLC

(57) ABSTRACT

The invention relates to plasmacytoid dendritic human cell lines and methods for producing the cell lines. More specifically, the invention relates to the plasmacytoid dendritic human cell line called GEN2.2, which is deposited in the CNCM under number CNCM 1-2938 and the plasmacytoid dendritic human cell line called GEN3, which is deposited in the CNCM under number I-3110. The use of cells from the cell lines is also disclosed.

10 Claims, 7 Drawing Sheets

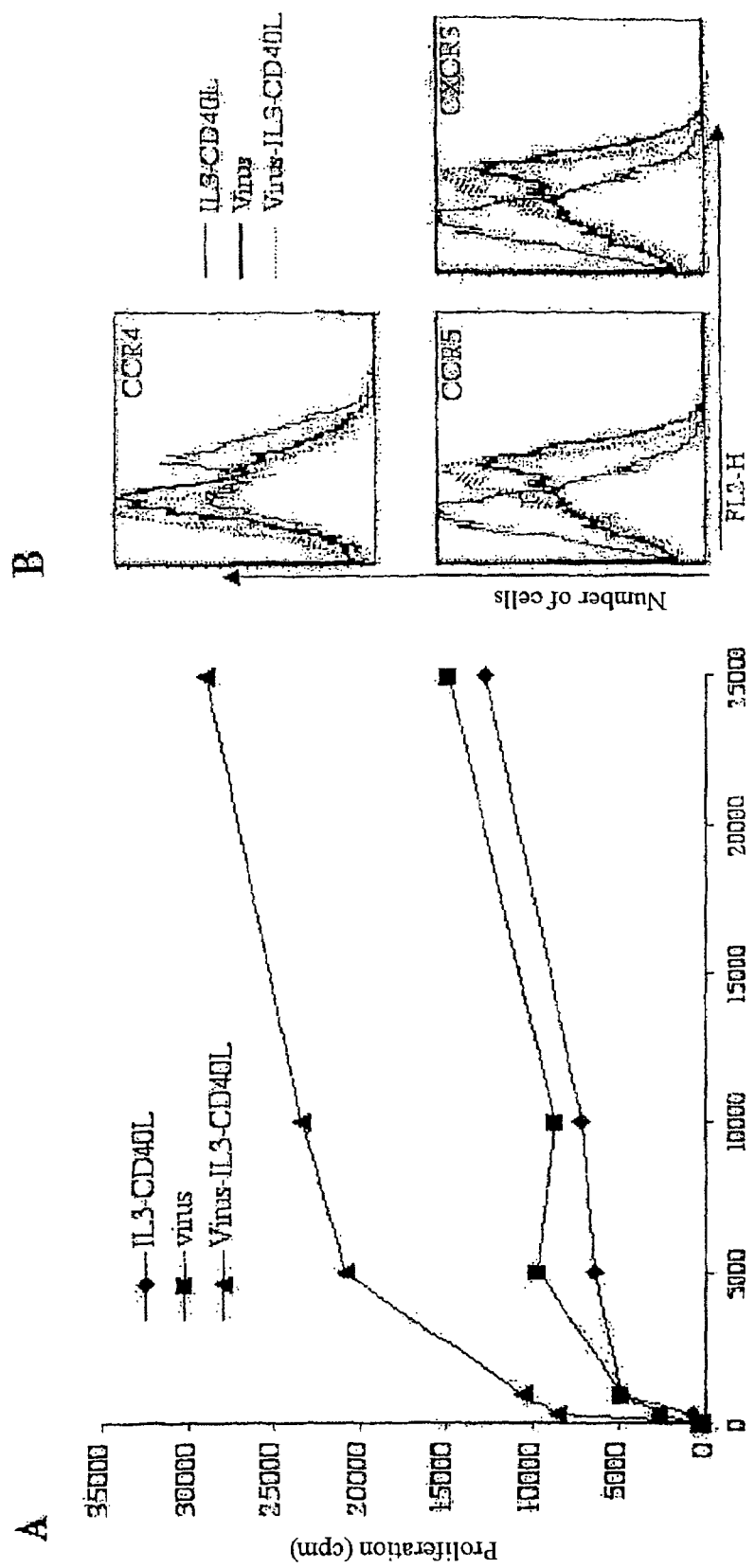
Fig. 4A + 4B

DENDRITIC CELL LINE

The present invention relates to human plasmacytoid dendritic cell (pDC) lines, and to the methods for obtaining and for culturing these cells. The invention also relates to the uses of these cells and to pharmaceutical compositions comprising these human plasmacytoid dendritic cells (pDCs).

Dendritic cells are key protagonists in the immune response: they are responsible for capturing antigens and processing them for the purpose of presenting them to T lymphocytes. Various dendritic cell precursors have been isolated from the blood; they express HLA-DR and CD4, in the absence of any other line-specific marker. Among these precursors, the most well characterized are of myeloid origin, expressing CD11c, CD13 and CD33 molecules, and differentiate (inter alia) into Langerhans cells; these cells are also called DC1. Another population of precursors, CD11c−, characterized by a very high level of expression of the IL3 receptor (CD123) has, moreover, been identified, and is itself also capable of differentiating into mature dendritic cells under the effect of IL3, or in the presence of a virus; they are called DC2, or plasmacytoid dendritic cells (pDCs).

pDCs were identified specifically from tonsils in 1997 by G. Grouard et al. (G. Grouard et al., J. Exp. Med., 1997; 185:1101-1111); they have also been described in the blood (O'Doherty U. et al., Immunology, 1994;82:487-493; Robinson S P. et al., Eur. J. Immunol., 1999;29:2769-2778), in the lymph nodes (Cella M. et al., Nat. Med., 1999;5:919-923) and in the thymus (Res P C. et al., Blood., 1999;94: 2647-2657; Bendriss-Vermare N. et al., J. Clin. Invest., 2001;107:835-844). These cells are characterized by their plasmacytoid-type morphology and their phenotype. pDCs express CD4, HLA-DR and CD45RA molecules, and lack the myeloid-type markers CD11c and CD13 (Cella M. et al., Nat. Med., 1999;5:919-923) or line-specific markers such as CD3, CD14 and CD19, although expression of CD2, CD5 or CD7 has sometimes been observed (Cella M., et al., Nat. Med., 1999;5:919-923; Res P C. et al., Blood., 1999;94: 2647-2657). More recently, it has been possible to identify the lectin BDCA2 specifically expressed by pDCs; BDCA4 is found on pDCs, but is also present on monocyte-derived DCs (Dzionek A. et al., J. Immunol., 2000;165:6037-6046 and Human Immunology, Vol. 63, 2002, pages 1133-1148). An argument in favor of these cells belonging to the lymphoid line is the fact that they express mRNAs encoding the chains preTalpha (Res P C., et al., Blood., 1999;94:2647-2657), lambda like 14.1 and SpiB (Bendriss-Vermare N., et al., J. Clin. Invest., 2001;107:835-844). These cells very strongly express the IL-3 receptor and weakly express the GM-CSF receptor (Cella M. et al., Nat. Med., 1999;5:919-923; Rissoan M C. et al., Science., 1999;283:1183-1186) and these two cytokines promote the survival of pDCs (Grouard G. et al., J. Exp. Med., 1997;185:1101-1111; Kohrgruber N. et al., J. Immunol., 1999;163:3250-3259; Robinson S P. et al., Eur J. Immunol., 1999;29:2769-2778), which otherwise die very rapidly in vitro. The costimulatory molecules CD80 and CD86 are absent or weakly expressed (Grouard G. et al., J. Exp. Med., 1997;185:1101-1111) and, at the immature stage, these cells are incapable of activating T lymphocytes (Kohrgruber N. et al., J. Immunol., 1999;163:3250-3259). On the other hand, in the presence of IL-3, of CD40L or of a virus, mature pDCs strongly express secondary antigen-presenting molecules (CD40, CD80, CD86 and HLA-DR) and then become as powerful as DCs of myeloid origin for activating allogenic T-cell proliferation (Kohrgruber N. et al., J. Immunol., 1999;163:3250-3259; Grabbe S. et al., Immunol Today., 2000;21:431-433; Kadowaki N. et al., J. Exp. Med., 2000;192:219-226). According to the stimulus responsible for their maturation (IL3 or virus), pDCs will polarize the response of the naive T lymphocytes that they activate, in a more or less strict manner, toward a Th1 or Th2 profile (Rissoan M C. et al., Science, 1999;283:1183-1186; Cella M. et al., Nat. Immunol., 2000;l:305-310; Kadowaki N. et al., J. Exp. Med., 2000;192:219-226).

Moreover, pDCs at the immature stage are responsible for the secretion of IFN-alpha detected in response to viruses (Cella M., et al., Nat. Med., 1999;5:919-923; Siegal F P et al., Science, 1999;284:1835-1837): they correspond to the "interferon producing cells" described in the 1980s. In addition, they are capable of responding to bacterial DNAs and to products of viral origin that they recognize since they express TLR7 (Ito T. et al., J. Exp. Med., 2002;195:1507-1512) and TLR9 (Bauer S. et al., Proc. Natl. Acad. Sci. USA, 2001;98:9237-9242) molecules. Normal pDCs therefore lie at the forefront of innate and adaptive immune responses, and could have a very important role in the initiation of antiviral responses.

Plasmacytoid dendritic cells (pDCs) open up new therapeutic perspectives since these cells are key protagonists in the immune response. Dendritic cells thus play an essential role in immune defenses with respect to infectious agents (bacteria, viruses, parasites), in immune defenses with respect to cancers, in allergic processes, in autoimmune responses, in the induction of tolerance and in transplant immunology. Dendritic cells are thus used in various therapeutic applications. Mention will in particular be made of cell therapy for cancers (Fong L. and Engleman E., Annu., Rev. Immunol., 2000; 18:245-273).

A major obstacle in the development of the various applications of plasmacytoid dendritic cells is the problem of isolating and purifying sufficient amounts of cells. Specifically, in humans, plasmacytoid dendritic cells (pDCs) represent less than 0.5% of the circulating cells, which makes it very difficult to isolate them from peripheral blood in large amounts. Moreover, the isolated cells do not proliferate in vitro and die rapidly in culture. Thus, no line of immortalized plasmacytoid dendritic cells (pDCs) is available at the current time. Only a dendritic cell line of myeloid and murine origin has been described (Winzler C. et al., J. Exp. Med., 1997;l85:317-328).

Chaperot et al. (Chaperot L. et al., Blood., 2001;97:3210-3217) have identified a new leukemia entity, involving a tumor-related equivalent of plasmacytoid dendritic cells. These cells were identified during investigations regarding CD4+ CD56+ leukemia tumor cells. In fact, these cells could not be classified in any of the leukemia categories described up until then. Chaperot et al. (Chaperot L. et al., Blood., 2001;97:3210-3217) put forward the hypothesis that these cells could belong to the pDC line. In fact, apart from CD56, the known phenotype of tumor cells could be superimposed on that of pDCs, in particular: CD4+, CD11c−, HLA-DR+, CD123+, CD45RA+. A functional study made it possible to show that, as for normal pDCs, IL3 and GM-CSF promote survival of the tumor cells in vitro. In addition, these tumor cells express mRNAs encoding the chains preTalpha and lambda like 14.1 and, in the presence of viruses, they are capable of secreting interferon-alpha. Furthermore, when the tumor cells are cultured in the presence of IL3, they undergo a very clear maturation, with a substantial increase in particular in the expression of the costimulatory molecules CD40, CD80 and CD86, and also the appearance of CD1a, CD1c and CD83. This maturation is accompanied by the acquisition of the ability to activate naïve T lymphocytes, which are then oriented toward a Th2-type cytokine production profile. The identification of leukemia-related pDCs offers new perspectives with regard to the phenotypic and functional characterization of normal pDCs. Specifically, they represent a source of cells that have the same characteristics as normal pDCs. However, the pathology remains rare, 23 patients having been identified by the GEIL: group d'études immunologique des leucémies [leukemia immunology study group] (Feuillard J. et al., Blood., 2002;99:1556-1563), and the recovery of large amounts of cells of quality is very difficult. In addition, the pDC cells taken from these patients do not naturally multiply in vitro, and methods for placing the cells in culture and for culturing them, in vitro, have not been described.

The aim of the present invention is therefore to propose an in vitro method for isolating a cell line of human plasmacytoid dendritic cells (pDCs). Any cell line thus obtained has many applications, in particular in the therapeutic field and in fundamental immunology.

DESCRIPTION OF THE INVENTION

The present invention relates to human plasmacytoid dendritic cell lines of phenotype CD4+, HLA-DR+, CD123+, CD45RA+, CD11c− and CD13−, and to the method for obtaining them.

The term "cell line" applies to mammalian cells cultured in vitro. Primary cultures of mammalian cells do not multiply in culture or cease to multiply in culture after a limited number of divisions. The cell lines according to the present invention are capable of multiplying indefinitely, something of which primary or secondary cultures of mammalian cells are incapable. These properties of the human plasmacytoid dendritic cell (pDC) lines according to the invention make it possible to advantageously obtain large amounts of cells by multiplication or proliferation of these cells in vitro. Preferably, the cell lines according to the invention are isolated after at least 20, 30, 40, 50, 60, 70, 80, 90, and preferably at least 100, cell divisions.

The plasmacytoid dendritic cell lines obtained according to the invention can therefore be described as immortal since they multiply indefinitely in vitro.

Plasmacytoid dendritic cells per se are known to those skilled in the art and can be identified by means of their morphological characteristics and by means of their surface phenotype. These morphological characteristics are an extended, endoplasmic reticulum-rich and therefore basophilic cytoplasm with an excentric nucleus which makes them resemble plasma cells (Siegal, Science, 1999, 284: 1835-1837, Grouard G. et al., J. Exp. Med., 1997). These plasmacytoid dendritic cell (pDC) lines are also characterized by means of their specific surface phenotype and in particular by means of the receptors/antigens expressed at the surface of these cells. Thus, the distinction of the various classes of immune system cells according to the receptors/antigens (cell markers) expressed at the surface of the cells is a technique that is widely described in the literature. These surface phenotype analyses are usually carried out by flow cytometry. Human plasmacytoid dendritic cells thus in particular express the CD4, HLA-DR, CD123 and CD45RA antigens. They lack the CD11c and CD13 markers specific for myeloid dendritic cells. The methods for identifying cells having this phenotype have in particular been described by M. Cella et al. (Nat. Med., 1999; 5:919-923).

The term "plasmacytoid dendritic cells" is therefore intended to mean cells that have the required morphological characteristics and a CD4+, HLA-DR+, CD123+, CD45RA+, CD11c−, CD13− phenotype.

Plasmacytoid dendritic cells characteristically express the BDCA2 and BDCA4 cell markers. The cells therefore have a BDCA2+, BDCA4+ phenotype.

A subject of the present invention is an in vitro method for isolating a human plasmacytoid dendritic cell line, comprising the steps consisting in:
a) culturing adherent stromal cells;
b) placing in culture leukemia tumor cells from a patient suffering from plasmacytoid dendritic cell leukemia, on said adherent stromal cells in a suitable culture medium; and
c) multiplying the cells by means of successive cell divisions on said adherent stromal cells in a suitable culture medium, so as to obtain a human plasmacytoid dendritic cell line.

A leukemia entity involving a tumor counterpart of human plasmacytoid dendritic cells has been described by Chaperot et al. (Blood, 2001;97:3210-3217). Preferably, the leukemia tumor cells placed in culture have a CD4+, HLA-DR+, CD123+, CD45RA+, CD11c−, CD13− phenotype. Preferably, these tumor cells also have a CD56+ phenotype. This phenotype can be detected according to known methods of the state of the art.

Preferably, the isolation of the line is carried out by placing in culture and culturing on adherent stromal cells of the MS-5 murine line.

Preferably, the steps consisting in placing leukemia tumor cells in culture and multiplying the cells by means of successive cell divisions so as to obtain a human plasmacytoid dendritic cell line are carried out in the presence of cytokines that support the proliferation and amplification of human hematopoietic cells.

Various cytokines that support the proliferation and amplification of human hematopoietic progenitors and cells can be used in the methods for isolating a plasmacytoid dendritic cell (pDC) line according to the invention. The amounts of cytokines to be used in the methods according to the invention are those that are conventionally used for cell cultures in vitro.

Preferably, the cells are placed in culture and multiplied in the presence of at least one cytokine chosen from the group comprising IL6, FLT3-L, SCF, IL3, IL7, G-CSF and GM-CSF. More preferably, the cells are placed in culture and multiplied in the presence of at least one cytokine chosen from the group comprising SCF and the FLT3-ligand.

Preferably, the cell lines according to the invention are established and isolated after at least 20, 30, 40, 50, 60, 70, 80, 90, and preferably at least 100, cell divisions.

In a particular embodiment of the invention, the in vitro method for isolating a human plasmacytoid dendritic cell line comprises an additional step (d) consisting in cloning the human plasmacytoid dendritic cell line obtained in step (c), so as to obtain various human plasmacytoid dendritic cell lines or "clones".

The "cloning of a line" denotes the individualization of cells of this line, and the culturing and multiplying of the individualized cells so as to obtain cell clones or lines. The term "clone" is intended to mean a collection of genetically identical cells obtained from a single cell.

In a particular embodiment, the in vitro method for isolating a human plasmacytoid dendritic cell line therefore comprises an additional step (e) consisting in selecting said various human plasmacytoid dendritic cell lines or clones, so as to identify the clones having a phenotype of interest.

According to a criterion of interest, the selection of variants having a particular characteristic may, for example, make it possible to study the role of a targeted molecule in the function of pDCs.

Among the various clones obtained from the multiplication of one cell, the clones of plasmacytoid human dendritic cells having a CD56+ or CD56− phenotype are thus, for example, selected.

Another subject of the present invention is an isolated cell line that can be obtained according to a method of the invention.

In a preferred embodiment, a subject of the invention is the human plasmacytoid dendritic cell line, called GEN2.2, deposited with the CNCM (Collection Nationale de Cultures de Microorganismes [National Collection of Cultures of Microorganisms], Pasteur Institute, 25 rue du Docteur Roux, F-75015 Paris) on Sep. 24, 2002, under the CNCM number I-2938 according to Rule 6.1 of the Treaty of Budapest, or a human plasmacytoid dendritic cell line, called GEN 3, deposited on Oct. 16, 2003, under the CNCM number I-3110 according to Rule 6.1 of the Treaty of Budapest.

Another subject of the present invention is a method for culturing and multiplying, in vitro, a human plasmacytoid dendritic cell line, comprising the steps consisting in:
  a) culturing adherent stromal cells; and
  b) culturing the human plasmacytoid dendritic cell line on said adherent stromal cells in a suitable culture medium.

The human plasmacytoid dendritic cell lines according to the invention are capable of multiplying indefinitely when they are cultured on adherent stromal cells. Various adherent stromal cell lines are known to those skilled in the art.

In the usual manner, the cells are cultured in plastic flasks, containers and dishes commonly used in this field, that allow the cells to adhere to the solid support. Advantageously, plastic flasks, containers and dishes are "precoated" or pre-seeded with adherent stromal cells.

In a particular embodiment, the stromal cells are cultured until confluency.

In an advantageous embodiment, the stromal cells are then irradiated in order to stop their proliferation, before beginning the culturing of the human plasmacytoid dendritic cell lines on said stromal cells.

The stromal cells are known to those skilled in the art. They are typically animal or human stromal cells derived from bone marrow or from other organs. Adherent stromal cells capable of supporting the proliferation of human progenitor cells are preferably used.

The adherent stromal cells are preferably chosen from the group comprising S17 stromal cells, AFT024 or M2-10B4 stromal cells (ATCC CRL 1972), HESS-5 stromal cells and MS-5 stromal cells (Itoh et al., Exp. Hematol., 1989; 17:143-147).

Advantageously, the adherent stromal cells are adherent stromal cells of the MS-5 murine line (deposited with the DSMZ [German Collection of Microorganisms and Cell Cultures] under the No. ACC441).

Culture media for culturing mammalian cell lines in vitro are well known to those skilled in the art and commonly used. Preferably, the usual culture media, such as RPMI 1640 Glutamax (GIBCO® culture media) supplemented with sodium pyruvate, nonessential amino acids and decomplemented fetal calf serum, are used.

Another subject of the present invention is an in vitro method for obtaining activated human plasmacytoid dendritic cells, characterized in that it comprises the following steps:

a) an isolated cell line according to the invention is provided;
  b) said cell line of step a) is activated so as to obtain activated human plasmacytoid dendritic cells.

Preferably, said cell line is activated with a virus and/or IL3 and/or CD40.

The methods for activating, in vitro, a human plasmacytoid dendritic cell line according to the invention make it possible to obtain a large number of activated or mature plasmacytoid dendritic cells. The present invention also relates to activated or mature human plasmacytoid dendritic cells obtained from the cell lines according to the invention.

Methods for activating plasmacytoid dendritic cells are known to those skilled in the art (Grouard G. et al., J. Exp. Med., 1997; Cella M. et al., Nat. Immunol., 2000;1:305-310). The activation or the maturation of the human plasmacytoid dendritic cell lines is therefore carried out according to usual techniques. Unlike the methods of the state of the art, the methods according to the present invention make it possible to obtain a large number of activated or mature cells by virtue of the use of human plasmacytoid dendritic cell lines according to the invention.

According to a first embodiment of the invention, the cell lines are activated with an enveloped or naked, single-stranded or double-stranded, RNA virus (for example, HIV, HTLV, influenza, mumps, measles, dengue and ebola) or DNA virus (for example, adenovirus, HSV, CMV, EBV), or derivatives thereof (poly-IC), with bacteria (for example, *M. tuberculosis*) or derivatives thereof (CpG ODN), or with parasites (for example, *leishmania*) or fungi (for example, *Candida albicans*)

Preferably, the activation is carried out in the presence of at least one virus chosen from influenza, HIV and HSV.

According to a second embodiment, the human plasmacytoid dendritic cell lines according to the invention are activated with stimuli of T lymphocyte origin, which are soluble factors such as cytokines (for example, IL3, GM-CSF or IFNα) or ligands that interact with surface receptors such as the proteins of the TNF family (CD40L or anti-CD40, for example).

Preferably, the human plasmacytoid dendritic cell lines according to the invention are activated with IL3 and/or CD40L.

According to a particularly advantageous embodiment, the human plasmacytoid dendritic cell lines according to the invention are activated with IL3, CD40L and a virus.

By way of example, the activation or the maturation of the plasmacytoid dendritic cell lines is induced by the addition of virus, of IL3-CD40L or of virus-IL3-CD40L to the culture medium.

The present invention also relates to any isolated, activated human plasmacytoid dendritic cell line that can be obtained according to any method described above.

Activated or mature human plasmacytoid dendritic cells are known to those skilled in the art and can be identified or detected according to usual techniques.

Typically, activated or mature human plasmacytoid dendritic cells secrete at least one molecule chosen from pro-inflammatory cytokines (for example, IL6, TNFα and IFNα), cytokines that orient the immune response (for example, IL12 and IFNα), chemokines (for example, IL-8, RANTES, IP10, MIG, MDC, TARC, I309) and antiviral cytokines (for example, IFNα).

Preferably, the activated (or mature) human plasmacytoid dendritic cells derived from cell lines according to the invention secrete at least one molecule chosen from IL12, TNF, IL6, IL8 and IFNα.

Conventionally, activated or mature human plasmacytoid dendritic cells are also characterized in morphological terms by means of numerous dendrites and by means of their phenotype. The maturation or the activation of the cells is thus accompanied by a large increase in the expression of HLA molecules of costimulatory molecules (for example, CD40, CD80, CD83, CD86) and of chemokine receptors (for example, CCR6 and CCR7). These cells then become capable of activating naïve T lymphocytes (Grouard G. et al., J. Exp. Med., 1997, Cella M. et al., Nat. Immunol., 2000;1:305-310, Rissoan M C. et al., Science., 1999;283: 1183-1186).

Preferably, the activated (or mature) human plasmacytoid dendritic cells derived from cell lines according to the invention express at least one cell marker chosen from HLA I, CD86, CD80, CCR6, CCR7 and CD83.

The cells derived from the activation or from the maturation of a cell line of plasmacytoid dendritic cells according to the invention exhibits at least one of the characteristics (secretion, morphology, phenotype, ability to activate naïve T lymphocytes) of activated or mature plasmacytoid dendritic cells.

The present invention also relates to a method for activating T lymphocytes, in vitro, characterized in that it comprises the following steps:
  a) an isolated cell line according to the invention is provided;
  b) said cell line of step a) is activated so as to obtain activated human plasmacytoid dendritic cells;
  c) T lymphocytes are brought into contact with said activated human plasmacytoid dendritic cells of step b).

Preferably, the cell line of plasmacytoid dendritic cells is activated with a virus, IL3 and/or CD40.

This method can be carried out on any type of biological sample comprising T lymphocytes. Preferably, it is a human or animal biological sample. The sample is preferably blood and, for applications of the immunotherapy and cell therapy type, it is autologous blood.

The present invention also relates to a method for identifying compounds that activate human plasmacytoid dendritic cells, comprising the steps consisting in:
  a) bringing the compound into contact with the plasmacytoid dendritic cell line according to the invention;
  b) detecting the activation of said cell line.

The detection of the activation or of the maturation of the human plasmacytoid dendritic cells is carried out according to conventional techniques known to those skilled in the art.

In one embodiment, the secretion of at least one molecule chosen from pro-inflammatory cytokines (for example, IL6, TNFα and IFNα), cytokines that orient the immune response (for example, IL12 and IFNα), chemokines (for example, IL-8, RANTES, IP10, MIG, MDC, TARC, I309) and antiviral cytokines (for example, IFNα) is detected.

Preferably, the secretion of at least one molecule chosen from IL12, TNF, IL6, IL8 and IFNα is detected.

In another embodiment, the increase in expression of HLA molecules, of costimulatory molecules (for example, CD40, CD80, CD86), of CD83 and of chemokine receptors (for example, CCR6 and CCR7) is detected.

The present invention also relates to a pharmaceutical composition comprising at least one cell of a plasmacytoid dendritic cell line according to the invention.

The plasmacytoid dendritic cell lines according to the invention are of therapeutic interest in the field of the antimicrobial and antitumor immune response.

The plasmacytoid dendritic cell lines according to the invention can be used in the treatment of various types of pathologies, in particular in the treatment of pathologies associated with infectious or microbial agents (bacteria, viruses, parasites, fungi), of cancers, of allergies and of autoimmune diseases.

More particularly, the plasmacytoid dendritic cells are capable of presenting tumor or microbial antigens in in vitro or ex vivo systems so as to induce an immune response against the tumor cells or the infected cells.

The present invention relates more particularly to the field of antitumor immunotherapy and cell therapy. The plasmacytoid dendritic cell lines according to the invention can thus be used as an immunotherapy agent.

The dendritic cell lines according to the invention are also used for producing a pharmaceutical composition, and advantageously for producing a composition capable of promoting an antitumor immune response for the treatment of cancers or an antimicrobial response for the treatment of infectious diseases.

The examples and figures below will make it possible to demonstrate certain advantages and characteristics of the present invention.

After the first 35 days of culture, a regular proliferation rate was obtained.

Each week, 0.6 million GEN2.2 cells were co-seeded with cells of the MS-5 line, and then diluted after 3 days. Two counts per week were performed. The theoretical cumulative number of cells was calculated from these counts.

Figure 2:
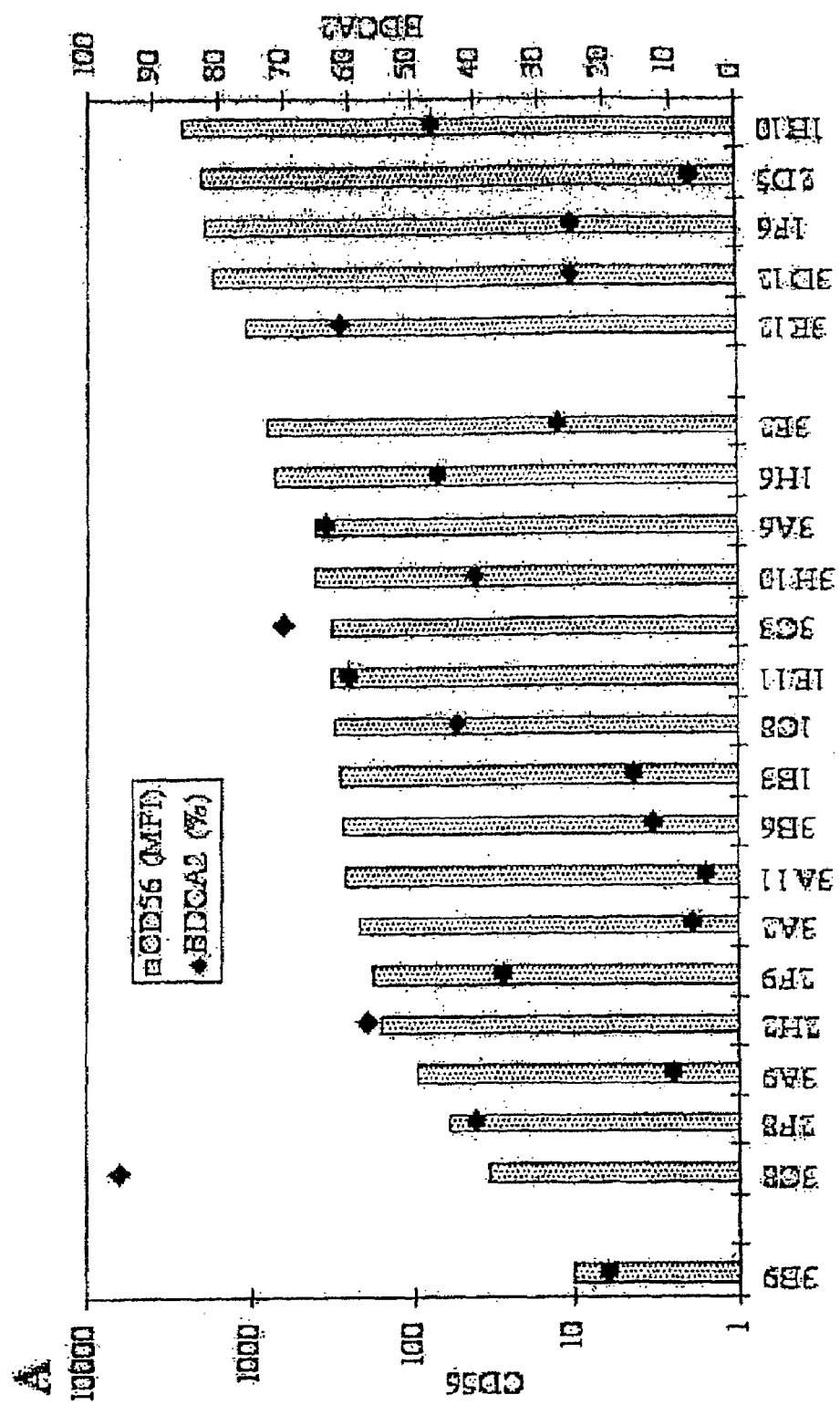
Figure 2:
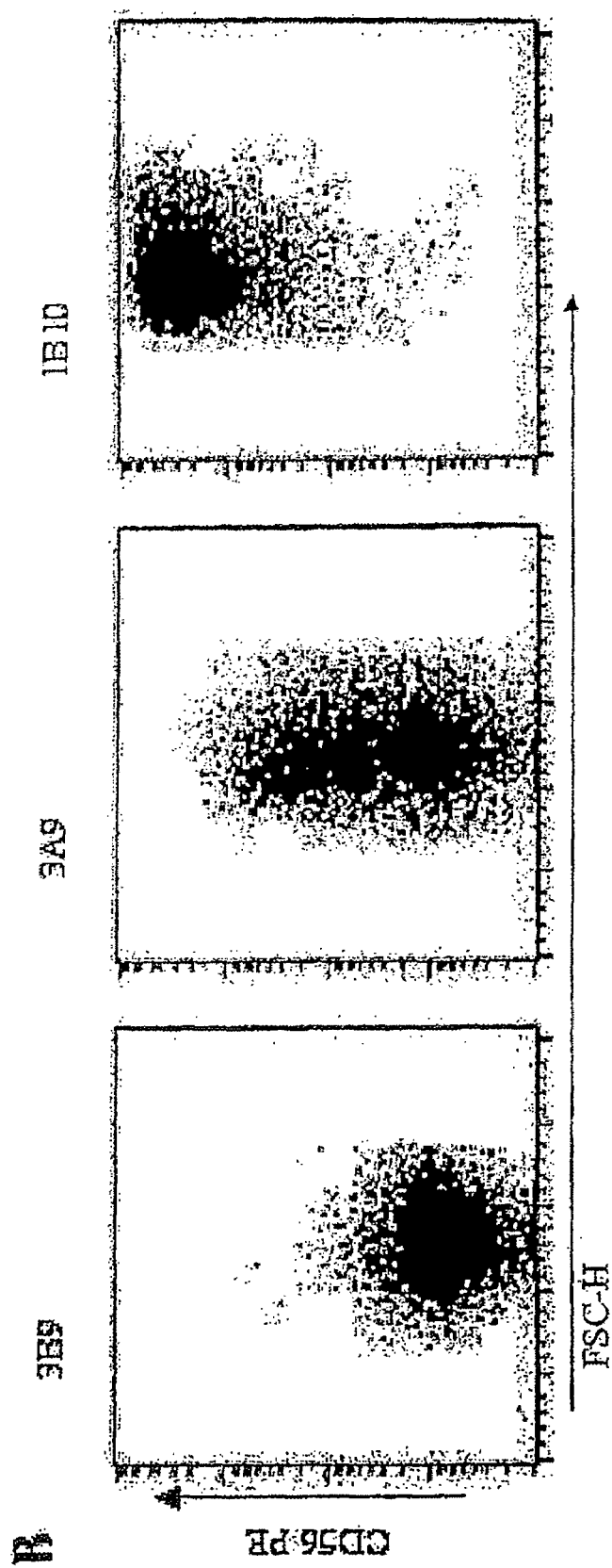

FIG. 2: Cloning of the GEN2.2 line

The 22 subclones of the GEN2.2 line obtained by limiting dilution express variable levels of CD56 and BDCA2 (flow cytometry measurement of the mean fluorescence or of the percentage of positive cells) (A). No correlation exists between the levels of expression of these two markers. Among the clones studied, 1 was negative for CD56 expression (3B9), 16 were heterogeneous (for example: 3A9), and 5 were very positive (for example: 1B10) (B).

Figure 3:
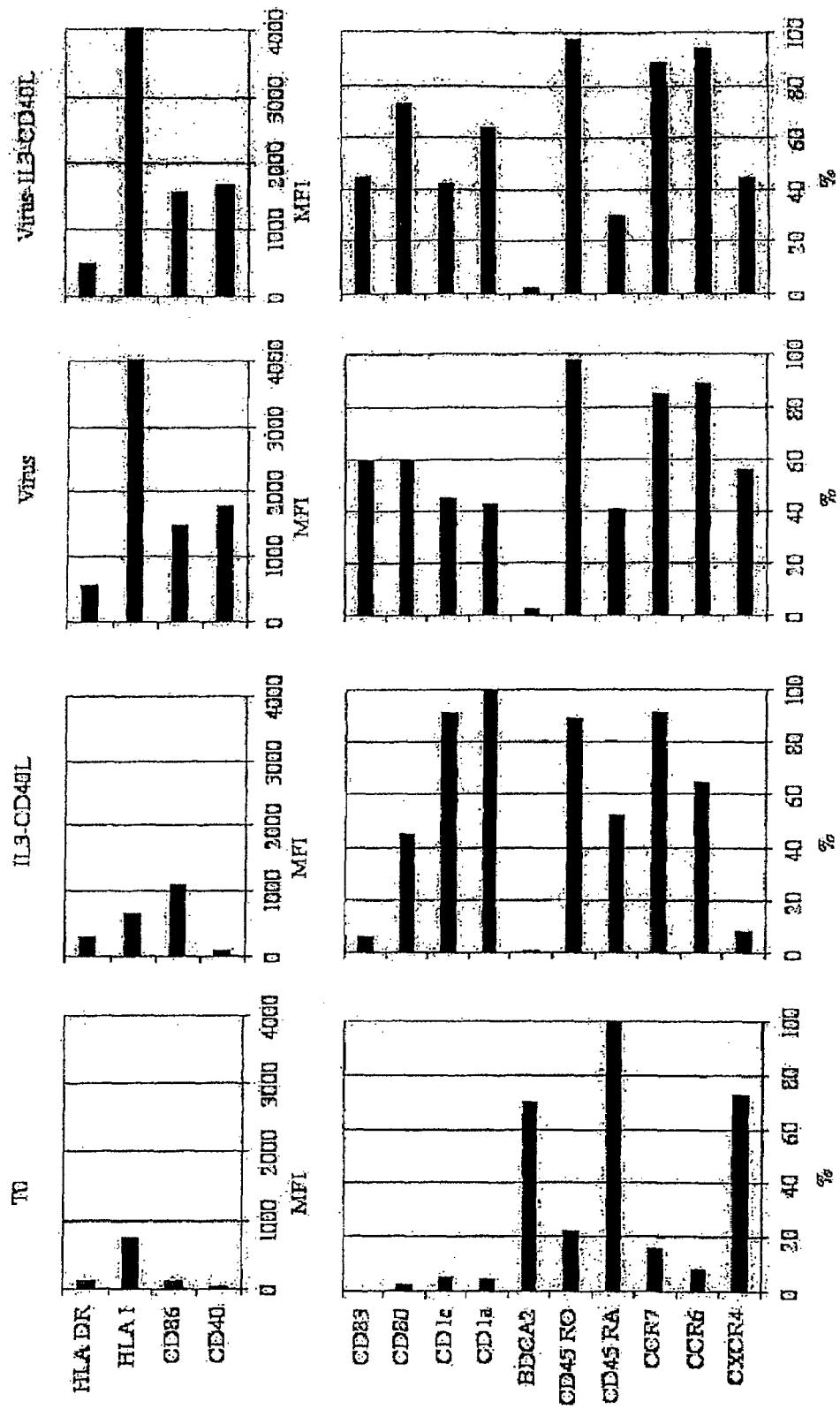

FIG. 3: Maturation of the cells of the GEN2.2 line

The cells of the GEN2.2 line were placed in culture for 48 h in the presence of IL3+CD40L, of influenza virus or of the three signals, and then phenotyped by flow cytometry. Under the three conditions, a clear maturation of the cells was observed, reflected by an increase in expression of the molecules associated with antigen-presenting functions (HLA I, CD40, CD80, CD86), and other modifications (increase in CCR6 and CCR7, decrease in CXCR4 and BDCA2).

Figure 4:
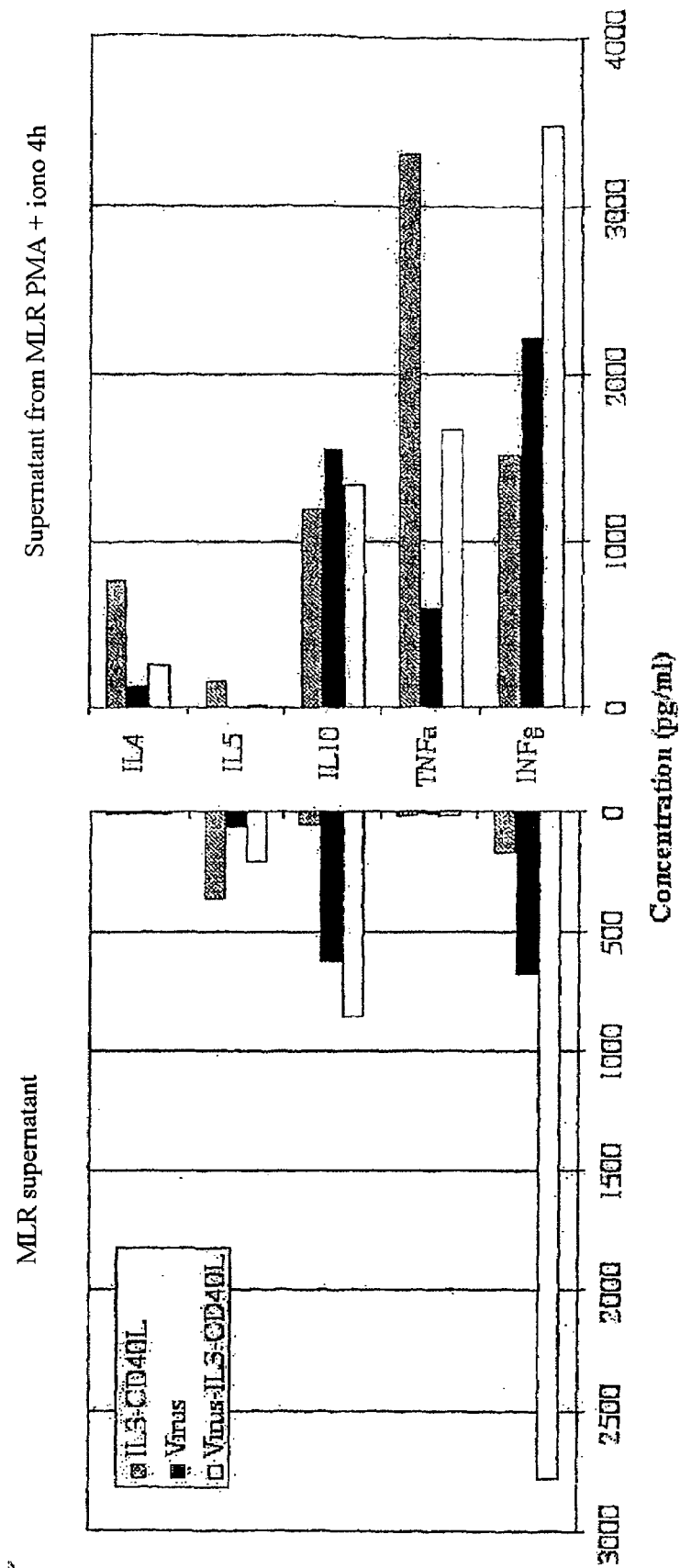
Figure 4:
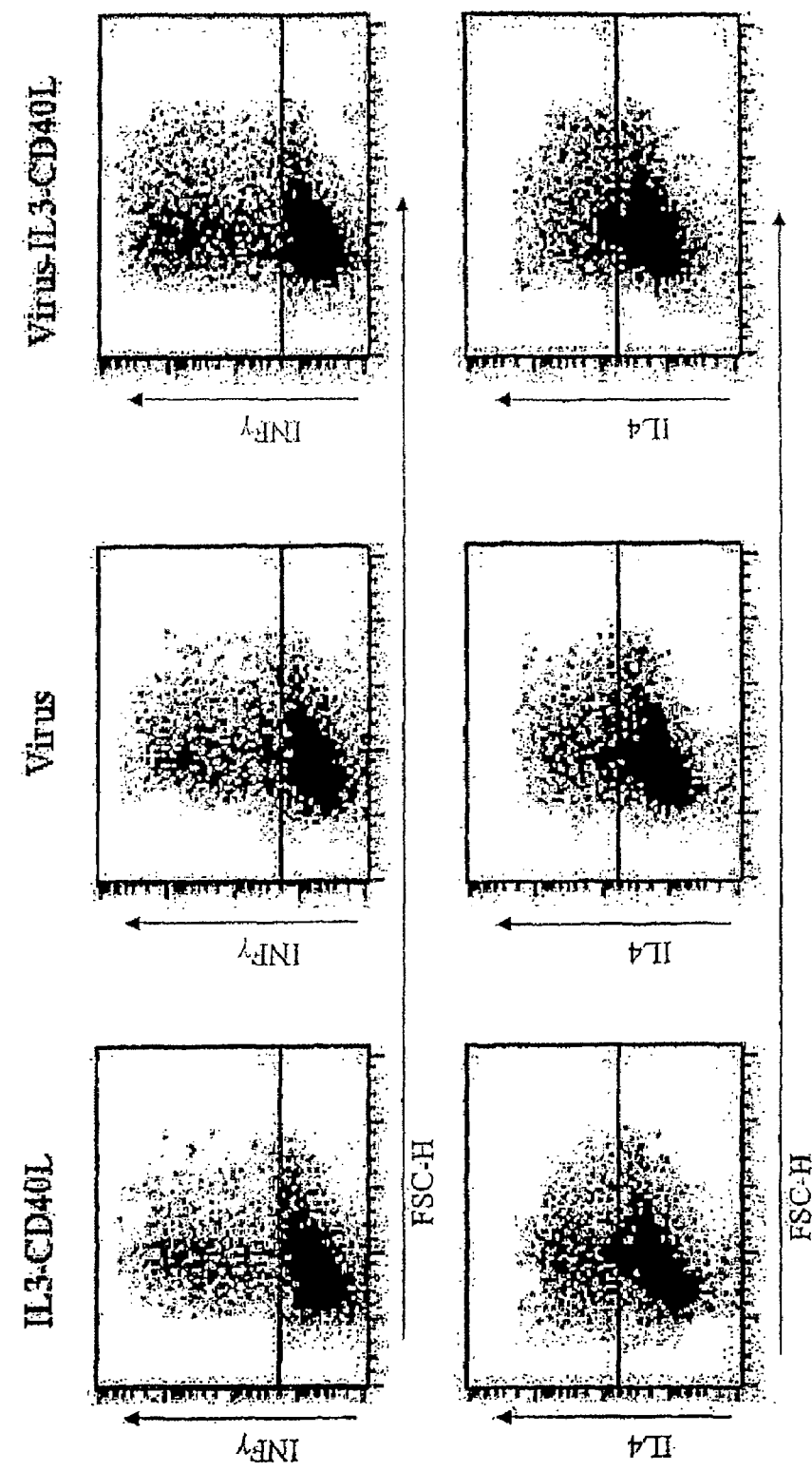

FIG. 4: Activation and Th1/Th2 polarization of naïve T lymphocytes

After 48 h of culture in the presence of IL3+CD40L, of virus or of the three signals, the cells of the GEN2.2 line were capable of inducing the proliferation of naïve CD4+ T lymphocytes (A).

The proliferation was measured by incorporation of triturated thymidine over 18 h, at the end of 6 days of mixed culture. The T lymphocytes activated in the course of this MLR express CCR4 if they have been activated with GEN2.2 cells preactivated in the presence of IL3+CD40L, whereas they express CCR5 and CXCR3 when they have been activated with cells of the GEN2.2 line preactivated in the presence of virus or virus+IL3+CD40L (B). The supernatants of the mixed culture and of the T lymphocytes reactivated at the end of the MLR with PMA+ionomycin exhibit more IFNg when the T cells have been activated with cells of the GEN2.2 line preactivated in the presence of virus or virus+IL3+CD40L, whereas more IL4 or more IL5 is found when the T cells have been activated with cells of the GEN2.2 line preactivated in the presence of IL3+CD40L (assaying by means of the CBA (Becton Dickinson) cytometry technique) (C). The detection of the percentage of cells secreting IFNg or IL4 was carried out after activation, with PMA+ionomycin, of the T lymphocytes at the end of the MLR. Fixed and permeabilized cells are labeled with antibodies specific for these cytokines and passed through the cytometer (D).

EXAMPLES

Example 1

Generation of a Human Line of Plasmacytoid Dendritic Cells

Figure 1:
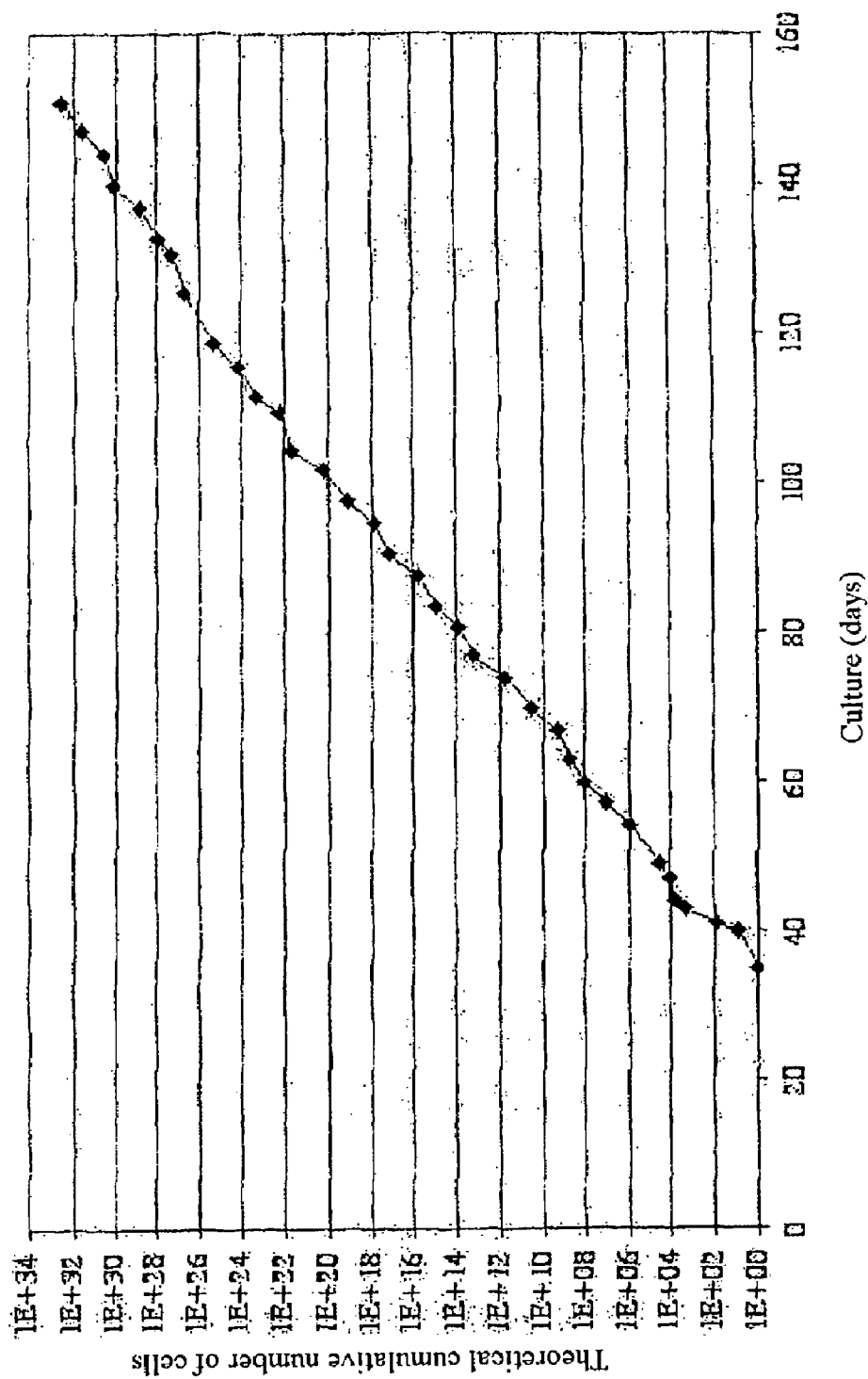
FIG. 1: Proliferation of the GEN2.2 line

The leukemia pDC cells were isolated from a sample of peripheral blood from the patient GEN previously described (Chaperot L. et al., Blood, 2001;97:3210-3217). The isolated mononuclear cells that were frozen contained more than 98% of tumor cells. The MS-5 murine adherent stromal line (Bennaceur-Griscelli A. et al., Blood, 1999;94:529-538; Issaad C. et al., Blood, 1993;81:2916-2924) was used as a "feeder". Five million tumor cells were placed in culture in a flask pre-coated with cells of the MS-5 line at confluency, in 5 ml of complete medium (RPMI 1640 Glutamax (GIBCO® culture media), supplemented with 1 mM of sodium pyruvate, 100 U/ml of penicillin, 100 µg/ml of streptomycin, nonessential amino acids, and 10% of decomplemented fetal calf serum). For the first five weeks of the culture, SCF (Nishi N. et al., Exp. Hematol., 1996;24:1312-1321) (stem cell factor) and Flt3-ligand (Pulendran B. et al., J. Immunol., 2000;165:566-572; Blom B. et al., J. Exp. Med., 2000;192:1785-1796) were added. The cells were counted and diluted with fresh medium containing the cytokines each week. At this stage of the culture, regular proliferation was obtained, and during the following four weeks, 0.6 million cells (then called GEN2) were co-seeded each week in a new flask with 0.6 million MS-5. The SCF and the Flt3-L were then eliminated, and the line continued to proliferate satisfactorily on the MS-5 sublayer; it was then called GEN2.2. This line could be maintained for at least 5 months in culture (FIG. 1). The doubling time of the line is 1.1 days. Irradiation of the MS-5 sublayer (60Gy) makes it possible to support in an identical manner the proliferation of the GEN2.2 line, while at the same time eliminating the contaminating MS-5 cells that could disturb certain functional analyses due to their proliferation. In the absence of MS-5, the GEN2.2 cells cease to proliferate and die.

Example 2

Phenotypic and Karyotypic Analysis of the GEN2.2 Line

The phenotype of the cells of the GEN2.2 line is determined by flow cytometry, using antibodies directly labeled with FITC or PE.

Like normal pDCs, the fresh cells of the GEN2.2 line are characterized by their expression of CD4, HLA ABC, HLA DR, CD45RA, CD123 (IL3-Ra), ILT-3, BDCA2 and BDCA4 (Table 1). CD7 is present, and 50% of the cells express CD56, whereas the other pan-T, B and NK markers are not detected (CD3, CD8, CD19, CD20, CD16, CD57).

The myeloid markers (CD13, CD11b, CD11c, CD14, CD64) are negative, whereas CD33 is positive. As regards the costimulatory molecules, the GEN2.2 cells express CD86, 27% are positive for CD40, whereas CD80 is absent. CD1a, CD1c and CD83 are not detected. The chemokine/homing receptors such as CCR1, CCR2, CCR3, CCR4, CCR5, CXCR1, CXCR2, CXCR5 and CLA are not expressed. CCR6 and CCR7 are found on 10 to 15% of the cells. More than 40% of the cells of the GEN2.2 line express CXCR3, CXCR4 and CD62L.

TABLE 1

| GEN2.2 cell phenotype | | | | | | |
|---|---|---|---|---|---|---|
| T/B cells | | | | | | |
| CD3 | CD4 | CD7 | CD8 | CD19 | CD20 | |
| 0 | 100 | 95 | 2 | 0 | 0 | |
| Myeloid/monocyte | | | | | | |
| CD13 | CD33 | CD11b | CD11c | CD14 | CD64 | CD116 |
| 2 | 66 | 2 | 10 | 0 | 1 | 25 |
| Natural killer cells | | | | | | |
| CD16 | CD56 | CD57 | | | | |
| 0 | 51 | 0 | | | | |
| Dendritic cells | | | | | | |
| CD1a | CD1c | CD83 | BDCA2 | BDCA4 | CD123 | ILT-3 |
| 4 | 5 | 2 | 70 | 88 | 100 | 100 |
| Antigen presenting cells | | | | | | |
| CD40 | CD80 | CD86 | HLA ABC | HLA DR | | |
| 27 | 2 | 100 | 100 | 100 | | |
| Misceallaneous | | | | | | |
| CD34 | CD36 | CD38 | CD45RA | CD45RO | CD65 | CD117 |
| 0 | 89 | 74 | 90 | 21 | 17 | 0 |
| Chemokine/homing receptors | | | | | | |
| CCR1 | CCR2 | CCR3 | CCR4 | CCR5 | CCR6 | CCR7 |
| 0 | 1 | 5 | 2 | 6 | 8 | 16 |
| CXCR1 | CXCR2 | CXCR3 | CXCR4 | CXCR5 | CLA | CD62L |
| 0 | 6 | 44 | 73 | 1 | 0 | 94 |

Among the 11 mitoses analyzed, 7 had the following karyotype 49,XY,+6,t(6:8)(p21;q24),+r(12),+20, and 4 had 49,iden,t(3;5)(q21;q21). This karyotype is identical to that of two subclones present in the initial tumor cells (patient UPN24) (Leroux D. et al., Blood, 2002;99:4154-4159).

Example 3

Subcloning of the GEN2.2 Line

A suspension of GEN2.2 cells was placed in culture on a confluent MS-5 sublayer, in flat-bottomed 96-well plates, in 0.2 ml of complete medium. 0.3 cell/well was deposited into two plates (called 1 and 2) and 1 cell/well was deposited into one plate (called 3). After 2 to 5 weeks of culture, the proliferating wells were transferred into 24-well plates, and then into culture flasks, always on an MS-5 sublayer.

19/96 wells grew in plate 3, and 12/192 grew in plates 1 and 2. 22 of these clones (10 of plates 1 and 2, and 12 of plate 3) were amplified, phenotyped and frozen. 5 of these clones strongly expressed the CD56 molecule (more than 99% of positive cells, with an MFI (mean fluorescence intensity) >1000); 1 clone does not express CD56 (less than 10% of positive cells, MFI<10); 16 clones exhibit heterogeneous CD56 expression (49 to 98% of positive cells, 33<MFI<800) (FIG. 2). All the clones are positive for HLA DR and CD4, and behave in the same way as the GEN2.2 line in terms of growth.

Example 4

Induction of the Maturation of GEN2.2 Cells with the Influenza Virus and/or IL3+CD40L The cells were cultured in complete medium, in the absence of MS-5, at 0.5 million/ml. Three culture conditions were evaluated:
"virus", in the presence of influenza virus (strain A/New Caledonia/20/99, subtype H1N1, Aventis Pasteur, $137 \times 10^{-3}$ µg of hemagglutinin/ml),
"IL3-CD40L", by addition of IL3 (10 ng/ml) and of recombinant soluble CD40L (1 µg/ml, Alexis),
"virus-IL3-CD40L".
After 48 h of culture, the culture supernatants were frozen for assaying off IFNα by ELISA (Beckman Coulter), and of ILL-β, IL2, IL4, IL5, IL-6, IL-8, IL-10, IL-12p70, IFN and TNF using the TH1/TH2 and inflammatory cytokine "cytometric bead array" (CBA, BD Bioscience) kits. The cells were recovered for phenotyping by cytometry, and cytospin smears with MGG staining.

As shown in FIG. 3, the cells of the GEN2.2 line mature when they are placed in culture in the presence of IL3-CD40L, of virus, or of the three signals. This maturation is reflected by a very clear increase in levels of expression of HLA I, CD86 and CD80 molecules, that are associated with antigen-presenting functions. The HLA-DR molecules also increase, but to a lesser extent. The expression of CD40 and CD83 is especially increased under the two conditions where the virus is present. The GEN2.2 cells also acquire CD1a and CD1c molecules, which are known to be expressed by myeloid-type DCs. Moreover, they loose BDCA2 under all these conditions, and also CXCR4. The expression of BDCA2 is in fact associated with an immature stage of DCs, allowing them to take up viruses (Dzionek A. et al., J. Exp. Med., 2001;194:1823-1834) and involved in the regulation of IFNα secretion. The loss of CXCR4, the ligand of which is SDF1, a molecule present in the secondary lymphoid organs, could suggest that the pDCs do not follow the same circulatory pathways as the myeloid DCs in returning to the lymph nodes; in fact, MDCs express CXCR4 only at the mature stage (Sallusto F. et al., Eur. J. Immunol., 1998;28:2760-2769). During their maturation, the GEN2.2 cells acquire CCR7, which could allow them to migrate to the secondary lymphoid organs where they could encounter the naïve T lymphocytes in order to activate them, this up-regulation also being described on DCs of myeloid origin (Sallusto F. et al., Eur. J. Immunol., 1998;28:2760-2769). The inversion of the CD45RA/RO ratio observed during the maturation of the cells, and also the acquisition of CCR6, are data that are not yet described on normal pDCs.

The supernatants of the cells activated with the virus contain TNFα, IL6, IL8 and IFNα. The secretion of these cytokines is zero or very low under the "IL3-CD40L" condition, but when the three signals are combined, the amount of TNFα, of IL6 and of IL8 detected is multiplied three-fold compared with the virus condition (Table 2), whereas the IFNα is unchanged, or slightly decreased. Entirely advantageously, IL12p70 is present under the "virus-IL3-CD40L" condition. This cytokine plays a very important role in the activation of Th1 lymphocytes and the differentiation of cytotoxic T lymphocytes that are fundamental in combating viruses. The production of IL12 by normal pDCs has been described by certain authors (Cella M. et al., Nat. Med., 1999;5:919-923; Cella M. et al., Nat. Immunol., 2000;1:305-310; Krug A. et al., Eur. J. Immunol., 2001;31:3026-3037), whereas many other studies have rather described their inability to produce this cytokine (Rissoan M C et al., Science., 1999;283:1183-1186; Ito T. et al., J. Exp. Med., 2002;195:1507-1512; Gilliet M. and Liu Y J., J. Exp. Med., 2002;195:695-704; Kadowaki N. et al., J. Exp. Med., 2001;194:863-869; Bauer M. et al., J. Immunol., 2001;166:5000-5007). We detected none of the other cytokines tested in the supernatants of these cells.

TABLE 2

| | Cytokines produced by the activated GEN2.2 cells | | | | |
|---|---|---|---|---|---|
| | IL12p70* | TNF* | IL6* | IL8* | IFNα+ |
| IL3-CD40L | 2 | 45 | 5 | 23 | 0 |
| Virus | 3 | 536 | 2391 | 391 | 1953 |
| Virus-IL3-CD40L | 190 | 1776 | 8690 | 2580 | 1657 |

*pg/ml, assay by the CBA technique
+IU/ml, assay by ELISA

Example 5

Th1/Th2 Polarization of Naïve T Lymphocytes

The cells of the GEN2.2 line were preactivated under the three conditions described in Example 4, in order to evaluate their ability to stimulate the proliferation of naïve T lymphocytes and to induce their differentiation along the Th1 or Th2 pathway. Naïve CD4+ T lymphocytes were purified from cord blood mononuclear cells using an immunomagnetic technique (stem cell technology). To measure the proliferation, 25 000 naïve T lymphocytes per well were stimulated with 25 000, 10 000, 5000, 1000 and 250 preactivated cells of the GEN2.2 line. Triturated thymidine incorporation was measured on the 6th day, over the last 18 hours of the culture. To evaluate the Th1/Th2 polarization, 50 000 naïve T lymphocytes per well were stimulated with 10 000 preactivated cells of the GEN2.2 line. After 6 days of culture, the culture supernatants were frozen and the recovered cells were phenotyped (CCR4, CCR5, CXCR3), and activated with phorbol myristate acetate (PMA 5 ng/ml)+ionomycin (0.5 µg/ml) for 4 hours or 6 hours in the presence of monensin (3 µM, Sigma) for the last 4 hours. IL2, IL4, IL5, IL10, TNFα and IFNγ were assayed in the supernatants, before and after activation with PMA+ionomycin for 4 h, using the Th1/Th2 CBA kit. The cells activated with PMA+ionomycin for 6 h in the presence of the secretion inhibitor were fixed (FACS Lysing solution, Becton Dickinson), and then permeabilized (FACS Permeabilizing solution, Becton Dickinson). The presence of Th1 or Th2 cells was detected by cytometry, with intracytoplasmic labeling using anti-IFNγ and anti-IL4 antibodies.

The greatest proliferation (25 000 cpm) of naïve CD4+ T cells was obtained with the cells preactivated under the "virus-IL3-CD40L" condition; the "IL3-CD40L" and "virus" preactivated cells are, however, capable of inducing naïve T cell proliferation (10 000 cpm), confirming the dendritic cell-type APC potentialities of the cells of the GEN2.2 line (FIG. 4A). In fact, only dendritic cells are capable of effectively activating naïve T cells. The polarization of the lymphocytes thus activated along the Th1 or Th2 pathways was evaluated according to several criteria.

First of all, the expression of CCR4, described as being associated with Th2 cells, is higher at the surface of the T cells activated with the "IL3-CD40L" cells, whereas the expression of CCR5 and CXCR3, described with regard to Th1 cells, is greater on the T cells activated with the "virus" and "virus-IL3-CD40L" cells (Sallusto F. et al., Immunol. Today., 1998;19:568-574) (FIG. 4B). Analysis of the cytokines in the culture supernatants shows that IL5 and IL4 (Th2 cytokines) are produced under the conditions where the T cells have been activated with the "IL3-CD40L" and "virus-IL3-CD40L" cells, whereas IFNγ (Th1) is especially detected under the "virus" and "virus-IL3-CD40L" conditions. IL10 is found in all the cases, possibly suggesting the presence of regulatory lymphocytes (Levings M K. et al., J. Exp. Med., 2001;193:1295-1302; Dieckmann D. et al., J. Exp. Med., 2001;193:1303-1310) (FIG. 4C). Confirming these results, the detection of intracytoplasmic cytokines shows a greater percentage of IFNγ-producing cells among the T cells activated with the "virus" and "virus-IL3-CD40L" cells, and a lower percentage of IL4-producing cells under the "virus" condition (FIG. 4D).

These results therefore show a preferential orientation along the Th2 pathway for the naïve T cells activated with the "IL3-CD40L" GEN2.2 cells, whereas a profile that is rather Th1 is induced with the "virus" cells, as has been described for normal pDCs (Rissoan M C. et al., Science, 1999;283:1183-1186; Cella M. et al., Nat. Immunol., 2000; 1:305-310; Kadowaki N. et al., J. Exp. Med., 2000;192:219-226). The "virus-IL3-CD40L" condition induces the strongest activation of T lymphocytes, orientating them rather toward a Th1 profile (CCR5+, CXCR3+, very strong production of IFNγ), with, however, the parallel differentiation of Th2 cells (production of IL4 and of IL5).

Example 6

GEN 3 Cell Line

The leukemia pDC cells were isolated from a sample of peripheral blood from the patient GEN previously described (Chaperot L. et al., Blood., 2001;97:3210-3217). The isolated mononuclear cells that were frozen contain more than 98% of tumor cells. The MS-5 murine adherent stromal line (Bennaceur-Griscelli A. et al., Blood., 1999;94:529-538; Issaad C. et al., Blood., 1993; 81:2916-2924) was used as a "feeder"; it is used after having been irradiated at 60 Gy. One million tumor cells were placed in culture in a flask precoated with 1 million cells of the MS-5 line, in 5 ml of complete medium (RPMI 1640 Glutamax (GIBCO® culture media), supplemented with 1 mM of sodium pyruvate, 100 U/ml of penicillin, 100 µg/ml of streptomycin, nonessential amino acids, and 10% of decomplemented fetal calf serum). The cells were counted and diluted with fresh medium each week, and regular proliferation was obtained. This line could be maintained for at least 3 months in culture. The line was deposited with the CNCM on 10/16/2003, under the number I-3110.

The invention claimed is:

1. A human immortal plasmacytoid dendritic cell line called GEN2.2, deposited with the CNCM under the CNCM number I-2938.

2. A human immortal plasmacytoid dendritic cell line called GEN3, deposited with the CNCM under the CNCM number I-3110.

3. A method for obtaining activated human plasmacytoid dendritic cells, in vitro, comprising:
   a) providing cells as claimed in claim 1; and
   b) activating the cells of step a) with viruses, parasites, fungi and/or stimuli of T lymphocyte origin to obtain activated human plasmacytoid dendritic cells.

4. The method as claimed in claim 3, characterized in that the cells are activated with a virus and/or IL3 and/or CD40.

5. A method for activating T lymphocytes, in vitro, comprising:
   a) providing cells as claimed in claim 1;
   b) activating the cells of step a) with viruses, bacteria, CpG-ODN, parasites, fungi and/or stimuli of T lymphocyte origin to obtain activated human plasmacytoid dendritic cells; and
   c) bringing T lymphocytes into contact with said activated human plasmacytoid dendritic cells of step b) to obtain activated T lymphocytes.

6. The method for activating T lymphocytes, in vitro, as claimed in claim 5, characterized in that, in step b), the cells are activated with a virus and/or IL3 and/or CD40.

7. A method for identifying compounds that activate human plasmacytoid dendritic cells, comprising:
   a) bringing a compound into contact with cells as claimed in claim 1; and
   b) detecting whether the cells are activated.

8. A method for obtaining activated human plasmacytoid dendritic cells, in vitro, comprising:
   a) providing cells as claimed in claim 2; and
   b) activating the cells of step a) with viruses, parasites, fungi and/or stimuli of T lymphocyte origin to obtain activated human plasmacytoid dendritic cells.

9. A method for activating T lymphocytes, in vitro, comprising:
   a) providing cells as claimed in claim 2;
   b) activating the cells of step a) with viruses, bacteria, CpG-ODN, parasites, fungi and/or stimuli of T lymphocyte origin to obtain activated human plasmacytoid dendritic cells; and
   c) bringing T lymphocytes into contact with said activated human plasmacytoid dendritic cells of step b) to obtain activated T lymphocytes.

10. A method for identifying compounds that activate human plasmacytoid dendritic cells, comprising:
   a) bringing a compound into contact with cells as claimed in claim 2; and
   b) detecting whether the cells are activated.

* * * * *